(12) United States Patent
Efinger et al.

(10) Patent No.: US 8,317,683 B2
(45) Date of Patent: Nov. 27, 2012

(54) ENDOSCOPE

(75) Inventors: Andreas Efinger, Rietheim (DE); Hans-Peter Eisele, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 911 days.

(21) Appl. No.: 12/389,079

(22) Filed: Feb. 19, 2009

(65) Prior Publication Data

US 2009/0209825 A1  Aug. 20, 2009

(30) Foreign Application Priority Data

Feb. 19, 2008  (DE) .......................... 10 2008 009 912

(51) Int. Cl.
*A61B 1/00* (2006.01)
(52) U.S. Cl. ........ 600/138; 600/128; 600/130; 600/133; 600/176; 600/182
(58) Field of Classification Search .......... 600/127–130, 600/133, 138, 160–16, 171, 175–176, 182
See application file for complete search history.

(56) References Cited

U.S. PATENT DOCUMENTS

| | | | |
|---|---|---|---|
| 4,747,661 A | | 5/1988 | Ohkuwa |
| 5,190,028 A | * | 3/1993 | Lafferty et al. ............... 600/129 |
| 5,331,948 A | * | 7/1994 | Utsumi et al. ................ 600/121 |
| 5,333,603 A | * | 8/1994 | Schuman ...................... 600/108 |
| 5,704,899 A | * | 1/1998 | Milo ............................. 600/161 |
| 5,871,440 A | * | 2/1999 | Okada .......................... 600/129 |
| 6,322,498 B1 | * | 11/2001 | Gravenstein et al. ......... 600/120 |
| 6,565,506 B2 | * | 5/2003 | Ishizuka ....................... 600/139 |
| 6,635,010 B1 | * | 10/2003 | Lederer ........................ 600/171 |

FOREIGN PATENT DOCUMENTS

| | | |
|---|---|---|
| DE | 19523959 A1 | 1/1996 |
| DE | 19822167 A1 | 12/1999 |
| DE | 20015447 U1 | 12/2000 |
| DE | 10314288 A1 | 10/2004 |
| EP | 1834575 A1 | 9/2007 |

OTHER PUBLICATIONS

European Search Report; EP 09 00 1283; May 18, 2009; 6 pages.

* cited by examiner

*Primary Examiner* — Matthew J Kasztejna
(74) *Attorney, Agent, or Firm* — St. Onge Steward Johnston & Reens LLC

(57) ABSTRACT

An endoscope having a hollow shaft for inserting an image guide, so that the distal end of the shaft is configured at an angle to the longitudinal axis of the shaft and the shaft is closed at the distal end by means of an end piece provided with a pass-through borehole for the image guide. To create an endoscope with an image transmission system of sufficient image size and image quality that can be autoclaved for cleaning purposes, it is proposed with the invention that the image guide should be positioned in the shaft in such a way that the bending radius of the image guide in the area of the bending of the shaft is greater than the bending radius of the shaft in the area of the bending.

10 Claims, 3 Drawing Sheets

ENDOSCOPE

CROSS-REFERENCE TO RELATED APPLICATIONS

The present application claims priority of German patent application No. 10 2008 009 912.0 filed on Feb. 19, 2008, the content of which is incorporated herein by reference.

FIELD OF THE INVENTION

The invention relates to an endoscope having a hollow shaft for insertion of an image guide, where the distal end of the shaft is configured so that it is at an angle to the longitudinal axis of the shaft and the shaft on the distal end is closed by means of an end piece provided with a pass-through borehole for the image guide.

BACKGROUND OF THE INVENTION

Endoscopes of this kind, configured as rigid endoscopes whose distal point is configured at an angle to the longitudinal axis of the shaft, are used, for instance, as sinuscopes for examining paranasal cavities and sinuses. The distal angle of the instrumental shaft is determined by the particular medical application.

The disadvantage of endoscopes of this type known from the art with angled distal shaft point is that they cannot be autoclaved for cleaning purposes, either because, at conditions of sufficient image size and image quality of the images produced by the image guide, high temperatures can cause breakage of the image guide, or else in the use of flexible image guides or image guides of small diameter, such endoscopes can in fact be autoclaved but leave something to be desired with respect to the image size and/or image quality.

It is consequently the object of the invention to create an endoscope of the aforementioned type so that with sufficient image size and image quality of the image transmission system it can be autoclaved for cleaning purposes.

SUMMARY OF THE INVENTION

This object is met by the invention in manner whereby the image guide is positioned in the shaft in such a way that the bending radius of the image guide is larger in the area of the bending of the shaft than the bending radius of the shaft in the area of the bending.

As a result of the arrangement of the image guide parallel to the axis inside the endoscope shaft, it is possible to arrange the image guide inside the endoscope shaft in such a way that the bending radius of the image guide is greater in the area of bending of the shaft than the bending radius of the shaft in the area of bending and thus also the bending stresses that arise on the image guide with respect to the arrangement of the image guide parallel to the axis that is known from the art can be clearly reduced in such a way that an endoscope configured according to the invention can be autoclaved without endangering the image guide even when using image guides that ensure sufficient image size and high image quality.

According to a preferred embodiment of the invention it is proposed that the image guide should be configured as a semi-flexible image guide in order to be able to follow the shaft bending even with a relatively large image guide cross-section.

To make it possible for the image guide to extend the large bending radius also in the field of its storage in the distal end piece of the shaft, it is proposed according to a practical embodiment of the invention that the pass-through borehole for the image guide in the end piece should be configured diagonally to the center axis of the shaft.

For insulating and protecting the image guide, it is further proposed that the image guide should be mounted inside the shaft in a guide tube that is preferably configured as a metallic tube.

The examination area is observed by means of an objective lens that is positioned on the distal end of the image guide and consisting at least of one lens and that is advantageously configured as a transversal viewing eyepiece to compensate for the crooked position of the image guide in the area of the distal-end pass-through borehole. The transversal eyepiece in addition has the advantage that the viewing angle can be extended beyond the longitudinal direction, for instance to make portions of the examination area visible that are also situated further in the proximal direction.

In order, on the one hand, to fix the image guide in the guide tube and, on the other hand, to ensure that the bending stresses arising on the image guide are not transmitted to the objective lenses, it is proposed with the invention that the image guide and guide tube should be cemented together in the area of the distal end of the image guide, so that the image guide is advantageously not bent in the cementing area in order to be able to reduce the bending stresses in this section.

It is further proposed with the invention that the image guide and the objective should be cemented to one another.

Finally, it is proposed with the invention that the bending of the distal end of the shaft with respect to the longitudinal axis of the shaft should be preferably by 60 degree. This dimension for the bending of the endoscope shaft has proved particularly appropriate for examining the paranasal cavities and sinuses when the endoscope is configured as a sinuscope. Greater and lesser angles for bending are also possible, of course, in the context of the inventive design.

Further characteristics and advantages of the invention can be seen from the appended illustrations in which an embodiment of an inventive endoscope is depicted merely as an example, without restricting the invention to this embodiment.

DETAILED DESCRIPTION OF THE INVENTION

Figure 1:
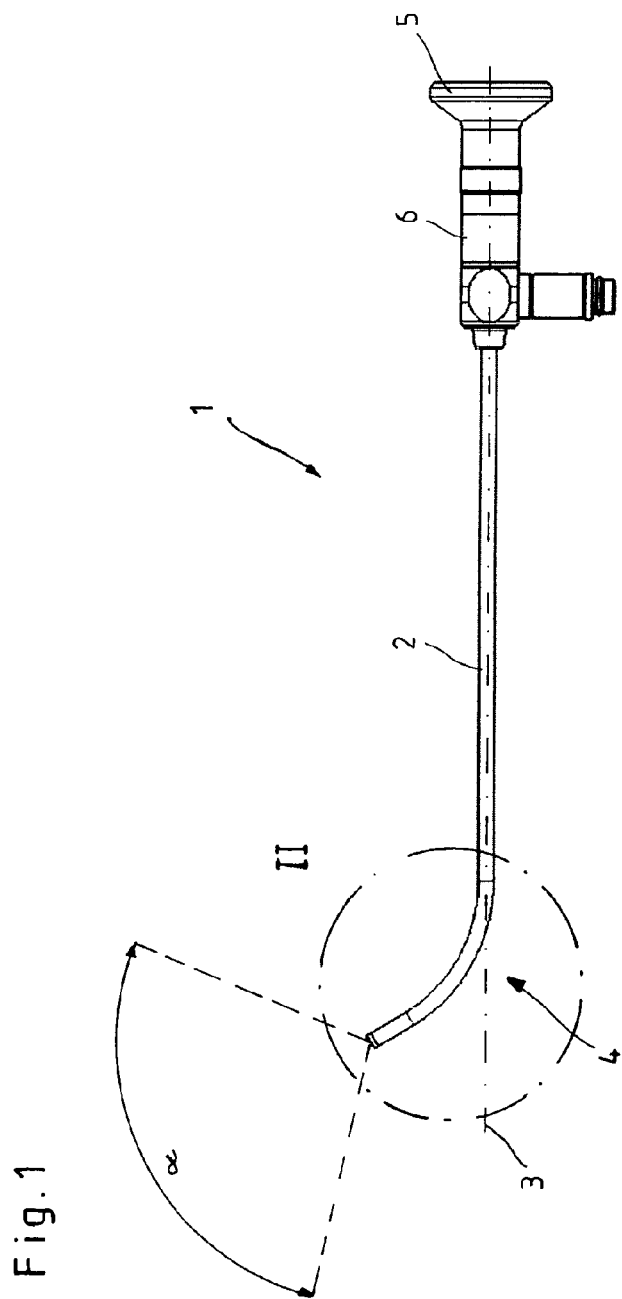
FIG. 1 shows a side view of an inventive endoscope.
Figure 2:
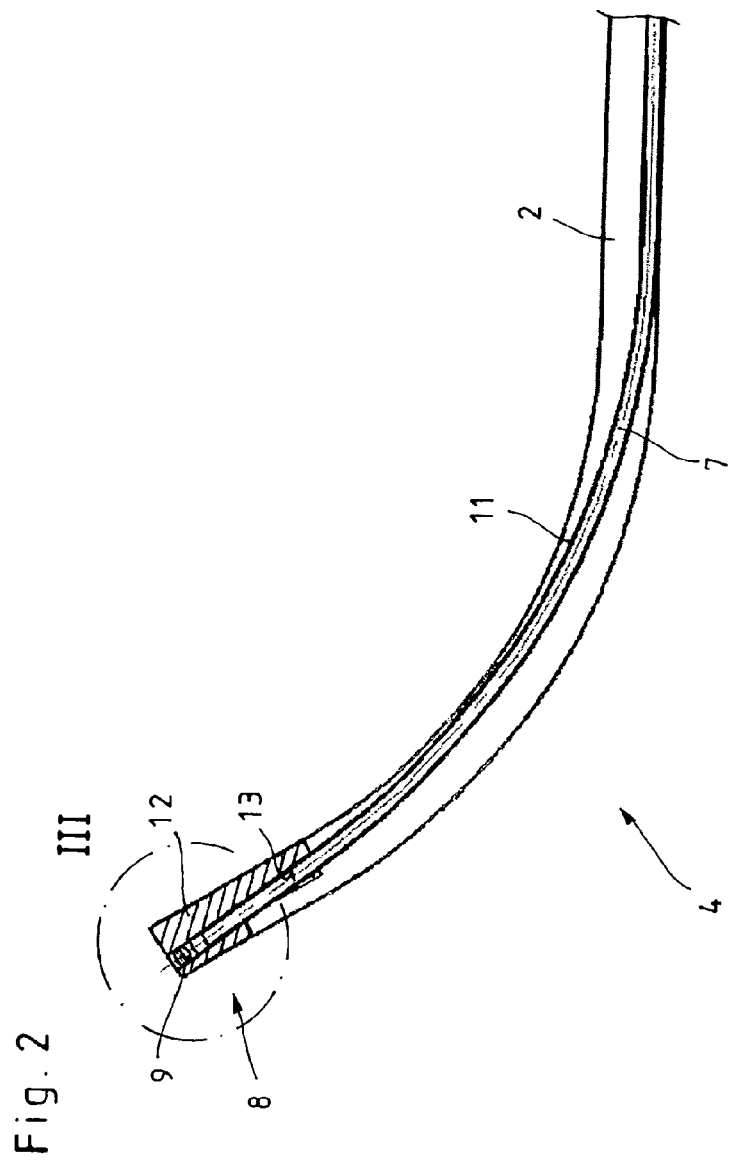
FIG. 2 shows an enlarged sectional depiction of detail II of FIG. 1.
Figure 3:
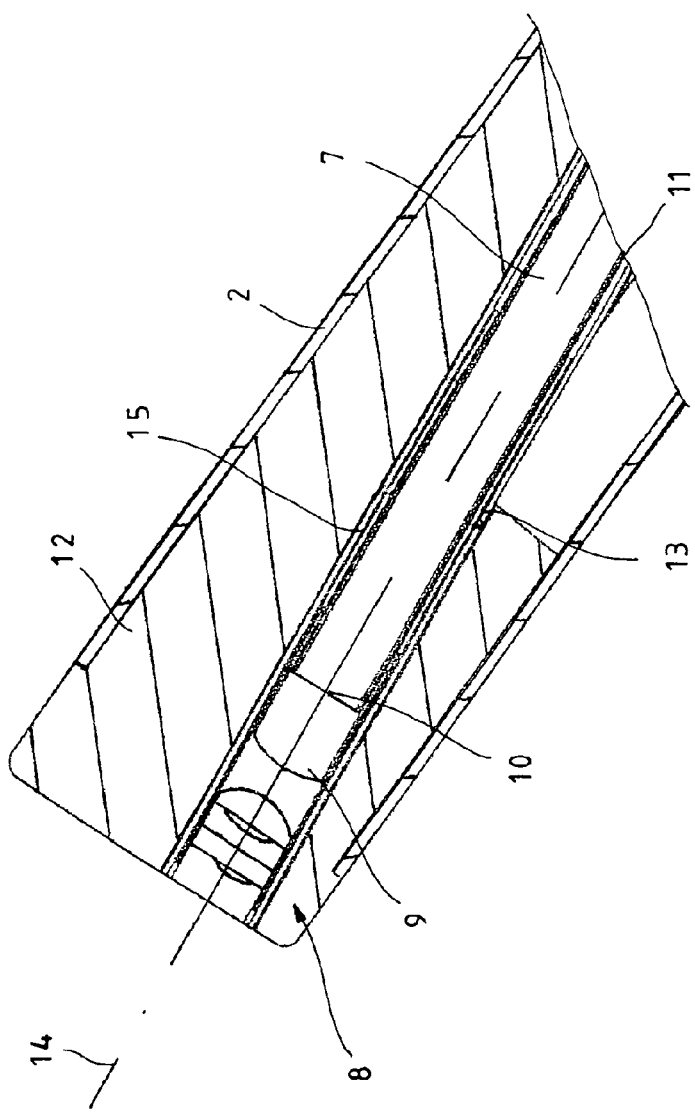
FIG. 3 shows an enlarged view of detail III of FIG. 2.

The endoscope 1 illustrated in FIGS. 1 through 3 consists essentially of a hollow shaft 2 whose distal end is configured as bent to form a lateral angle 4 with respect to the longitudinal axis 3 of the shaft 2. On the proximal end the endoscope 1 comprises a handle 6 provided with an eyepiece unit 5.

The illustrated endoscope 1 is a sinuscope for examining paranasal cavities and sinuses. The bending 4 of the shaft 2 with respect to the longitudinal axis 3 of the shaft 2 is determined medically on anatomical grounds in order to allow the endoscope 1 to be inserted into the examination area. It is advantageous for the angle to be of 60 degrees to the longitudinal axis 3, although other sized angles can also be configured for the bending 4.

As can be seen from the sectional views in FIGS. 2 and 3, an image guide 7 is positioned inside the shaft 2 and, for purposes of image transmission, connects the eyepiece unit 5 with an objective 8 that forms the distal end of the image guide 7. The objective 8, in turn consists in the illustrated embodiment of several individual lenses 9, so that the proximal end of the objective 8 and the distal end of the image guide 7 are cemented to one another on a contact surface 10. The image guide 7 here is a semi-flexible image guide 7, in order to make it possible to follow the bending 4 of the shaft 2 even when there is a relatively large image guide cross-section.

The use of flexible image guides 7 is a disadvantage because they produce a decidedly reduced image quality in comparison with semi-flexible image guides 7.

For insulating and protecting the image guide 7, the image guide 7 is mounted inside the haft 2 in a guide tube 11 preferably configured as a metallic tube.

On the distal end the shaft 2 is closed by an end piece 12, which is provided with a pass-through borehole 13 for inserting and storing the image guide 7 or the guide tube 11 complete with the image guide 7.

As can be seen from FIG. 2, the image guide 7, particularly in the area of the bending 4, is not positioned centered or otherwise as parallel to the axis of the central axis 14 of the shaft 2. The mounting of the image guide 7 in the shaft 2 is instead arranged in such a way that the bending radius of the image guide 7 in the area of the bending 4 of the shaft 2 is greater than the bending radius of the shaft 2 in the area of the bending 4. This greater bending radius on the part of the image guide 7 causes a clear reduction of the bending stresses exerted on the image guide in comparison with endoscopes known in the art, in which the image guide is mounted on a parallel axis in the shaft 2.

As a result of this reduction of the bending stress in the image guide 7, it is possible to autoclave the endoscope 1 for cleaning purposes, so that the endoscope is exposed to a temperature of more than 120 degrees C. without risk of damaging the image guide 7, particularly in the area of the cementing with the objective 8.

The displacement of the image guide 7 inside the shaft 2 with reduced bending stress not only makes the endoscope 1 autoclavable but also allows for the use of semi-flexible image guides 7 that have a relatively large guide cross-section so that the resulting image size is also advantageous for the operator.

The course of the image guide 7 that departs from parallelism with the axis inside the shaft 2, with the bending radius that is larger in comparison with the shaft 2, is brought about in the illustrated embodiment because the pass-through borehole 13 for the image guide 7 in the end piece 12 is configured as diagonal to the center axis 14 of the shaft 2, as can be seen from FIGS. 2 and 3.

The objective eyepiece 8 is advantageously configured as an oblique-view eyepiece 8 to compensate for the crooked position of the image guide 7 in the area of the distal-end pass-through borehole 13. In addition the oblique-view eyepiece has the advantage that the viewing direction can be expanded beyond the longitudinal directionin order, for instance, to make areas of the examination area visible that are also situated farther in the proximal direction. A customary viewing angle alpha for the objective 8 is illustrated as an example in FIG. 1 at more than 90 degrees.

In order, first, to fix the image guide 7 in the guide tube 11 and, second, to ensure that bending stresses arising in the image guide 7 are not transmitted to the objective lenses 9, the image guide 7 and the guide tube 11 are cemented together in the area of the distal end of the image guide 7, so that the image guide 7 in the cemented area 15 is advantageously not bent, that is, is configured straight, in order to be able to reduce the bending stresses of the previous bending in this section.

An endoscope 1 of this configuration is distinguished in that, because of the displacement of the image guide 7 with minor bending stresses inside the shaft 2, it is possible to create an endocope 1 that has an image transmission system of sufficient image size and image quality and can be autoclaved for cleaning purposes.

What is claimed is:

1. An endoscope having a rigid hollow shaft for inserting an image guide, so that a distal end of the shaft is configured at an angle to a longitudinal axis of the shaft and the shaft is closed at the distal end by means of an end piece provided with a pass-through borehole for the image guide, wherein the image guide is positioned in the shaft in such a way that a bending radius of the image guide in an area of the bending of the shaft and in a direction of the bending of the shaft is larger than a bending radius of the shaft in the area of the bending, and wherein the pass-through, borehole for the image guide in the end piece is configured diagonally to the center axis of the shaft.

2. The endoscope according to claim 1, wherein the image guide is configured as a semi-flexible image guide.

3. The endoscope according to claim 1, wherein the image guide is positioned in a guide tube inside the shaft.

4. The endoscope according to claim 3, wherein the guide tube is configured as a metallic tube.

5. The endoscope according to claim 3, wherein the image guide and the guide tube are cemented together in the area of the distal end of the image guide.

6. The endoscope according to claim 1, wherein an objective consisting of at least one lens is positioned on the distal end of the image guide.

7. The endoscope according to claim 6, wherein the objective is configured as an oblique-view eyepiece.

8. The endoscope according to claim 6, wherein the image guide in an area where it is cemented to the guide tube is configured without bending.

9. The endoscope according claim 6, wherein the image guide and the objective are cemented together.

10. The endoscope according to claim 1, wherein the bending of the shaft on the distal end describes an angle preferably of 60 degrees to the longitudinal axis of the shaft.

* * * * *